United States Patent [19]

Herscu

[11] Patent Number: 5,797,839
[45] Date of Patent: Aug. 25, 1998

[54] HOMEOPATHIC TREATMENT SELECTION SYSTEM AND METHOD

[75] Inventor: Paul Herscu, Amherst, Mass.

[73] Assignee: Apple Blossom, LLC, Amherst, Mass.

[21] Appl. No.: 772,415

[22] Filed: Dec. 23, 1996

[51] Int. Cl.[6] .................................................. A61B 5/00
[52] U.S. Cl. .............................................................. 600/300
[58] Field of Search .................... 600/300; 128/920–925; 434/262

[56] References Cited

U.S. PATENT DOCUMENTS

| | | | |
|---|---|---|---|
| 5,463,548 | 10/1995 | Asada et al. | 600/300 |
| 5,619,990 | 4/1997 | Kanai | 600/300 |
| 5,619,991 | 4/1997 | Sloane | 600/300 |

OTHER PUBLICATIONS

Homeovia, "Welcome to Radar Homeopathic Software", http://www.homeovia.com/radar/intro.html, pp. 1–11, Jul. 1996.

*Primary Examiner*—John P. Lacyk
*Assistant Examiner*—Samuel Gilbert
*Attorney, Agent, or Firm*—Choate, Hall & Stewart; Sam Pasternack; Brenda H. Jarrell

[57] ABSTRACT

A system and method for assisting a homeopath in the diagnosis and selection of treatments for a patient. The system includes a digital computer adapted to store information related to symptoms and remedies for symptoms. The computer is adapted, via a program, to assist the homeopath in case-taking by prompting the homeopath for collection of symptoms by providing case-taking suggestions. The computer is further adapted via the program to group symptoms into segments, and to facilitate the homeopath in building a cycle of segments. The segments are utilized to index into the stored information to select remedies for the symptoms incorporated into the segments. The system is further adapted to interact with the homeopath in the selection of which particular symptoms go into a particular segment.

10 Claims, 8 Drawing Sheets

HOMEOPATHIC TREATMENT SELECTION SYSTEM AND METHOD

FIELD OF THE INVENTION

This invention is related to computer systems which facilitate the selection of medical treatments stored in a database of a information system. More particularly, the invention is related to an information system for the selection of homeopathic treatments stored in a database.

BACKGROUND OF THE INVENTION

History and Definitions

Homeopathy was developed by Samuel Hahnemann in 1790. While he was translating a materia medica from english into german, he came across a reference that the prevalent prescription for malaria at that time was cinchona bark. The reason stated for its efficacy it stated was that it was quite bitter. Dr. Hahnemann was well versed in the current use of medicine and decided there must be another reason besides its bitter qualities that made it work. He reasoned that other medicines were bitter but were not useful in the treatment of malaria. To prove his point, he experimented on himself by taking cinchona bark and observed the effect. Within a short time he experienced chills, fever, palpitations, sweats, in short, all the symptoms of malaria. He wrote down these effects in the text that he was translating as a footnote.

The more he studied and translated medicine and medical texts, the more he observed this phenomenon. If healthy people took massive amounts of a particular drug, the drug would actually cause the same symptoms it was supposed to cure. Hahnemann began to wonder what would happen if you matched the symptoms of a sick patient to symptoms that a drug produced. He began experimenting with this method and developed a new branch of medicine, which he called homeopathy. This is actually the definition of homeopathy, homeo, meaning the same, and pathos, meaning illness.

Hahnemann and some of his healthy colleagues, while in a healthy state, began taking many of these drugs to find their effects on the healthy. They carefully recorded and collated the symptoms that each drug produced. This testing and recording of a homeopathic drug on healthy people is called a proving. Provings are recorded and collated, and then assembled together in a reference text called a materia medica.

The current materia medicas have up to 5,000 proven drugs listed. The drugs are derived from plants, minerals and animal substances. The remedies are listed in alphabetical order in the materia medica. The materia medica has grown to include not just symptoms that were proven but also to include toxicological symptoms as well as symptoms that were actually cured in sick patients using that particular remedy. The symptoms in the materia medica are categorized in order from the top of the body on down. So all the symptoms in the head are categorized together, then the eyes, ears, nose and so on until the extremities.

Some remedies have only 40 symptoms listed in the materia medica, while others have 15,000 symptoms. Since it is impossible to remember all the symptoms of each remedy, about 150 years ago the information was collated into a reference form. All the remedies that affect a certain place in a certain way were placed under a particular category. The book that contained these categories is called a repertory. The categories listed in the repertory are called rubrics.

The repertory of the materia medica is actually a reference tool that lists all the symptoms cured or produced and list every remedy that has treated that particular category/rubric. For example, a rubric might list: Head: pain, above left eye, 3pm lasting to 6pm, with one remedy listed under the rubric. Rubrics can be very specific like this one, or very general. A general rubric would be Head; pain, and that general rubric would contain hundreds and hundreds of remedies. The more specific the rubric the better for a homeopath, as it truly indicates a closer match. However, specific rubrics are likely to be too specific and incomplete and therefore misleading.

Over the years, there have been many changes and additions to the repertories. Ten years ago, repertories were computerized into several, databases to speed up the search process. Six or seven years ago, an expert system was added to one of the databases to further help with remedy selection by setting certain guidelines that will then give more weight to some rubrics and less weight to other rubrics.

Essentially, homeopathy is a very simple medicine to practice. You simply try to match perfectly the symptoms of the patient to a remedy. There are, however, a few difficulties. For instance, it's impossible to match all the symptoms of a patient to a remedy. Mathematically speaking, it stands to reason that when all the patient's symptoms are included the remedies with 15,000 rubrics will come up more often than those with only 50. This means that the repertory has a natural leaning to show the large remedies as the right remedies if you take into account each and every symptom the totality.

It then becomes a question of taking the logical totality of a patient. In other words, which symptoms shall practitioner consider that truly represent the whole disease state of the patient.

The hardest part of homeopathy then is in the symptom selection. Depending on how you select your symptoms, you will either be led to the correct or incorrect remedy. There can only be one correct remedy at a time for a patient.

There are several theories on how to select the appropriate symptoms, but there are no clear designations of when to use which theory, so one is left with confusion as to which symptom to choose at any one time.

The Method for Selection of a Remedy

The method a homeopath practices for selection of remedy is broken down into several parts.

1. The patient comes to the homeopath to be treated. The homeopath will spend up to 90 minutes eliciting the symptoms that the patient. This is called the anamnesis or case taking.

2. The symptoms are then analyzed and the homeopath decides which symptoms to try to match.

3. The homeopath tries to translate the words that the patient spoke into symptoms/rubrics listed in the Repertory.

4. The homeopath then tries to find which remedies were listed in the greatest number of rubrics listed in the repertory. Steps 3 and 4 are called the process of Repertorization.

5. The homeopath then reads the materia medica for a full description of any of the remedies that ran through all the rubrics and are in consideration.

The homeopath makes the final remedy selection based on the reading of the materia medica The homeopath then prescribes that remedy to the patient and the visit is ended.

Difficulties with the Repertory

Historically, homeopathic philosophy says you must match the symptom of the drug with the symptom of the patient. However, there are a few problems with the theory.

First of all, the patient's words might be difficult to match to the original proving language. For instance, a patient may say, "when I have a headache, I'm in a funk," or, "When I have diarrhea I blow off work." What does this mean? How does a homeopath relate these words to the proving language that may have been written 200 years ago.

Another problem is that the remedy you are looking for may not be listed in the appropriate rubric, because the remedy has not been proven well enough. In addition, there are numerous mistakes in the repertory which further complicate the database that is used. And lastly, it often requires several years of careful study and practice to understand how to elicit the necessary information to prescribe upon.

To summarize the problems are 1) it's difficult for the homeopath to elicit the information, 2) it's hard for a homeopath to know if he or she has elicited enough information from the patient, 3) incomplete remedy proving prevents listing of the preferred remedy, 4) there are errors in the repertory, and 5) underlying language difficulties.

Thus, it is an object of the present invention to provide a computer system to facilitate the selection of homeopathic remedies.

It is an additional object of the invention to provide a computer system for facilitating the selection of symptoms for a treatment.

It is an object of the invention to provide a computer system containing homeopathic rubrics and treatments.

It is also an object of the invention to provide a computer system to assist the homeopath in eliciting information from the patient.

It is an additional object of the invention to provide a computer system to assist the homeopath in knowing when the homeopath has enough information.

It is a further object of the invention to provide a computer system that is capable of modifying the database homeopathic treatments.

Other objects and advantages of the subject invention will be apparent to those skilled in the art from consideration of the attached drawings and the detailed description set forth below.

SUMMARY OF THE INVENTION

This invention is related to computer systems which facilitate the selection of medical treatments stored in a database of a information system. More particularly, the invention is related to an information system for the selection of homeopathic treatments stored in a database. The invention assists the homeopath in case-taking, remedy selection and treatment. The system utilizes a predefined database of homeopathic information and facilitates case-taking by prompting the homeopath for additional information based upon a state of the case-taking. The system facilitates remedy selection by focusing the homeopath on the cycle of the disease and selecting remedies based upon such a model. The system facilitates treatment by allowing a historical record to be kept of each patient thus allowing the homeopath to track the course of disease and modify the treatment accordingly.

One embodiment of the present invention is a computer-implemented method for facilitating the selection of remedies for a patient, the computer containing an input unit, a display unit, and a database providing a data file containing a plurality of indexed data records containing symptoms, rubrics, segments and remedies. The database contains the symptom data records that further contain indications of rubrics, rubric data records that further contain indication of remedies, and segments segment data records containing an indication of rubrics within the segment.

The system carries out the steps of building a set of rubrics until receiving a completion indicator via the steps of first receiving via the input unit a first set of input data identifying patient symptoms. Next, receiving via the input unit a first command to create at least one rubric from the symptoms followed by creating the at least one rubric by indexing via the database into the data file for the symptom data records matching the first set of input data and reading the indications of rubrics in the symptom data record. Then collecting the at least one rubric into the set of rubrics.

The system further is adapted to receive, via the input unit, a second command to create at least one segment from the set of rubrics via the steps of indexing via the database into the data file for rubric data records matching the rubrics in the set of rubrics and reading the indication of segments in the rubric data records, and creating via the database an at least one segment data record containing at least a portion of the rubric data records.

The system is further adapted to identify at least one remedy by indexing via the database into the data file for remedy data records related to the at least a portion of the rubric data records in the at least one segment.

BRIEF DESCRIPTION OF THE DRAWINGS

A preferred embodiment of the invention has been chosen for purposes of illustration and description and is shown in the accompanying drawings, forming a part of the specification, wherein.

DETAILED DESCRIPTION OF THE PREFERRED EMBODIMENTS OF THE SUBJECT INVENTION

Figure 1:
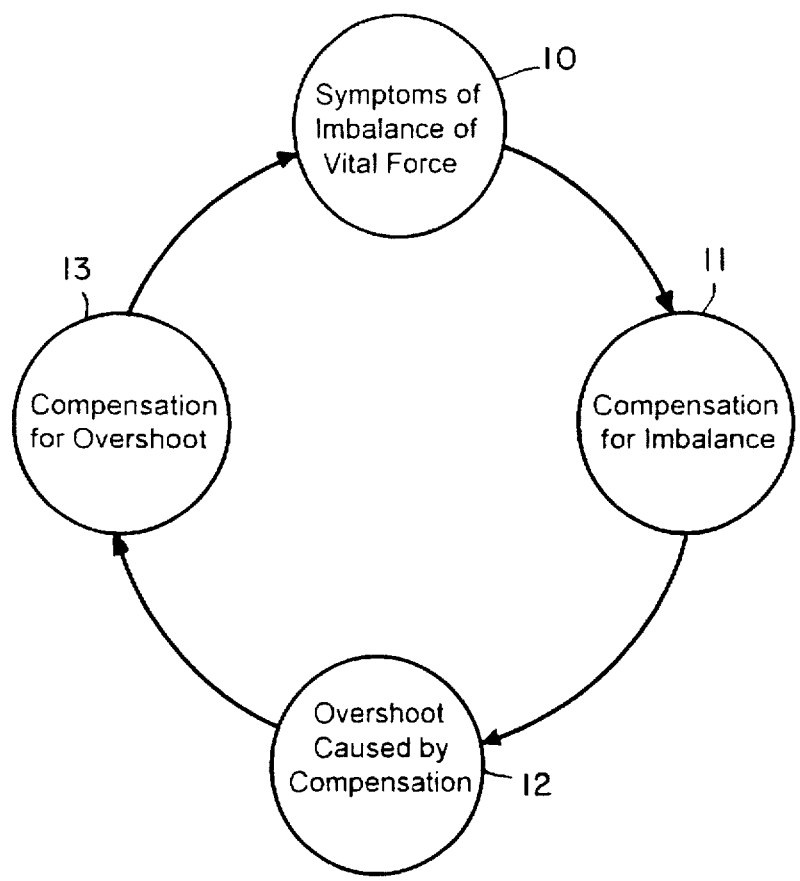
FIG. 1 is a block diagram illustrating the cycle of the vital force caused by an imbalance in the system.

We come into the world with a body and spirit and our vital force. It animates us and, in a sense, is us. But the health of that vital force will vary from one person to the next. From the moment of our conception, it is affected by various genetic as well as environmental factors. Then along comes a stress that the person is susceptible to, and the vital force is overwhelmed and knocked out of balance. And that's how disease begins.

Disease is a unit. It is one disease for one person at one time. It begins in a single place (usually the individual's weakest spot) but it also shows itself throughout the whole being in many ways, manifesting through many signposts which are called signs and symptoms. It is a homeopath's job is to ferret out that one disease for that one person. The vital force's job is to help us find it by producing signs, or symptoms, that show us the pattern of the disease.

How does the vital force do this? When it first gets 'untuned', it strains to adjust to the stress, in order to reestablish its balance. This straining is what produces the symptoms that point out the disorder and signal what is wrong. Another way of putting it is that the vital force, thrown off balance by the stress, no longer has the ability to cure. It is flawed. Its efforts fail. This failed attempt is itself the chronic disease illustrated in full color. Thus, the symptoms are not the disorder itself but in some way show the disorder, by mirroring it or embodying it.

How can a homeopath best see the message that the vital force is struggling so hard to show us? It is flashing the pathology of the whole patient, if only the homeopath could see it. Its message can be detected in every symptom of the patient. That is the genius of the vital force. It is doing a great job. If, by giving us dozens or maybe hundreds of examples, the vital force can say in a nutshell, "This is it. This is the disease," why can't we? What a help it would be if a homeopath could describe with a single statement every symptom that a remedy can produce or cure.

But there is a nagging question getting in the way. If there is only one disease, how do all the symptoms fit together? Not just most of the symptoms, not just the ones a practitioner selected, but all of the symptoms, the mental state, the sleep position, the food cravings and aversions, the common as well as the characteristic symptoms.

Until now, homeopaths have been forced to settle for the bulk of the symptoms and let go of the rest. They have learned several mechanistic models of understanding, and with trial and error eventually found success more and more. But here comes that nagging again: Why not every symptom? If the disease is throughout the being, then every single symptom, from unimportant ones to important ones, should in some way mirror that disease. So what can be done? Homeopaths need to understand and match not just the symptoms of the illness, but more importantly the way of being sick.

Another Voice

As T. S. Eliot said in his *Four Quartets*, "... next year's words await another voice." Although homeopathy has a strong vitalistic philosophy, that the practical application has often been mechanical at best. So, in order to create a more practical, effective, streamlined way of case taking and repertorization, new words must be found for saying what a practitioners have to say and new ways of saying it.

The present invention is a system and method of studying and practicing homeopathy. Using a common language this method could act as a matrix for classical homeopaths to express their different ways of teaching, prescribing, and writing. By so doing, they can add to each other's findings, thereby refining homeopathy and propelling it forward.

The present system involves formulating a phrase or sentence for each remedy that will substantially fit every symptom of that remedy, every patient treated who needed that remedy, every materia medica utilized, every lecture heard, and every live case as well as paper cases studied of that remedy. It must be a sufficiently precise phrase that sums up not only all that this remedy encapsulates, but also the dynamic aspect of it, how it moves from one stage of the illness to the next. For Stramonium such a sentence might be: Driven by confusion, fears, and vulnerability, Stramonium is engaged in an ongoing and violent battle between the unconscious and the conscious, between darkness and light, between succumbing to the death realm and yearning to exist in the life realm. Examined carefully, everything about Stramonium should fit this picture.

If a homeopath can begin to understand each remedy in the materia medica in this way, there will be much less need to memorize facts and facts and facts. This would be quite in line with the picture Hahnemann painted—a picture of the vital force putting on a show (for the purpose of preserving the patient). The vital force strains to shout out the plot. The symptoms are the main characters, not just bit players entering and exiting in some haphazard fashion. They move within a script in a logical pattern. It is this logical pattern that homeopaths have been trying to perceive all along.

This pattern is what Hahnemann meant when he spoke about a totality of symptoms. By totality he did not simply mean the total number of symptoms, but rather the total pattern of the disease. That is the real totality. The pattern is not as simple as being just mental or emotional or physical. It is a pattern of unfolding. It does not begin or end at any one point.

What is that unfolding, or movement? The vital force gets knocked off center by some stress. To correct that and re-establish a balance, it strains. As illustrated by FIG. 1, the strain shows itself in signs and symptoms 10. These symptoms grow stronger as the vital force compensates too much 11, until they finally overshoot the mark 12. The overshoot must be corrected 13 to maintain some semblance of balance. That, in time, brings the patient full cycle back to (or at least near to) where he started 10.

In this way the cycle is reinforced, over and over again. It is as if you are getting on a train trying to go directly to a certain destination. But the train instead makes a loop, stopping at various places along that loop and finally coming back to where you first began. This loop or cycle is the disease, and it keeps repeating itself over and over again. We will see this later in the Cycle of Stramonium.

How can the cycle ever be broken? A shift is needed in the underlying balance so that the patient can return to health. But change is hard to come by; it is easier to go on and on in the rut of the cycle. If you reflect upon your own life, you may recall times when you found yourself in somewhat of a 'stuck' mode, and you struggled to get free of it, but the more you tried to break the pattern or habit, the deeper you got into the rut.

The fluid action of chronic disease is like that. It first establishes a certain pattern and then renews itself by falling into the same groove over and over again, each time sinking deeper, spiraling downward. The deterioration shows up in the mental and emotional and physical spheres in different ways. This pattern, this cycle of events, will (in some way) be recognizable everywhere—in all the symptoms of the patient, in all the symptoms listed in the materia medica for that remedy, and in all the symptoms brought out in the provings.

If we can look at disease in this way, we will be better able to identify and isolate the main elements or ideas, which I call fundamental segments, within each of the remedies. That will allow us to recreate the chain of events showing the pattern that fits not only everything known about that remedy, but everything known about every patient who has ever needed it. It will even give us the freedom to predict the direction the disease will take.

The Fundamental Segments within the Cycle

Everything a homeopath observes in the patient is showing the same balancing act of the vital force. Every single symptom a person expresses is an example of one of the fundamental segments operating in that person's cycle of disease. This includes even our strong symptoms, our mental symptoms, our sleep symptoms, everything. Each one is an example. This explains why we get in trouble when we take the keynotes literally. That is, we think the person must desire sweets in order to fit Stramonium. But sweets is only an example of the yearning for comfort in this isolated and lonely person. In other words, a symptom does not stand alone. It has a relationship of some kind to other symptoms. And so, that desire for comfort or consolation, which is one of the fundamental segments of the remedy, will show up over and over again in many places and many ways through various symptoms. Some of these symptoms will be found in rubrics, some will not. That doesn't matter. It is the segment, the idea, that matters. That segment is something which absolutely belongs to that remedy.

Figure 2:
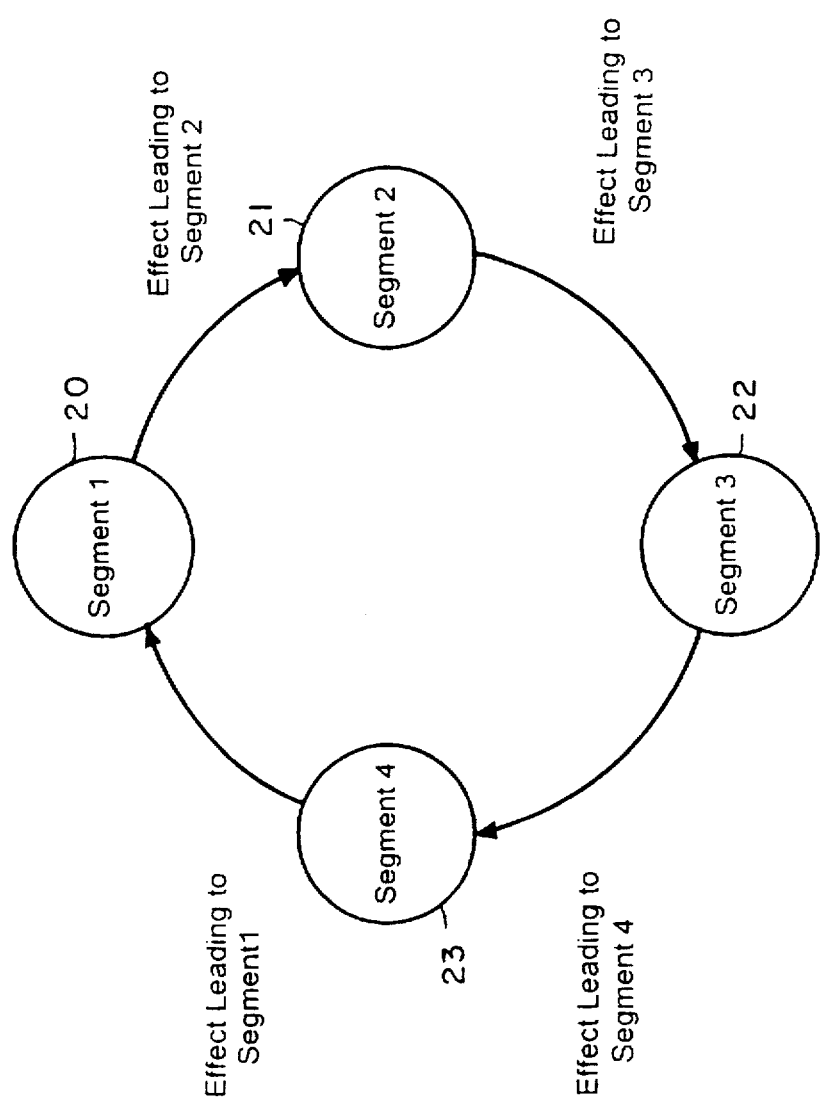
FIG. 2 is a block diagram illustrating the segments in a cycle of a disease connected by relationships between segments; components.

As illustrated by FIG. 2, the cycle itself is a flow of events that is composed of a number of fundamental segments, for instance 20, 21, 22 and 23. Each one of these segments could be described by a word or phrase, such as yearning for comfort or violent overreactions. In the model showing the cycle, you will see that each segment is linked by an arrow to the next segment, representing its direct effect leading to the one that follows. It in some way pushes the person to the next segment. Each segment flows into the next until you come full cycle again. The cycle is the disease. You can jump in at any point, start with any segment. The pattern is a continuous flow.

Another way of looking at it. Picture for a moment a circle of stepping stones surrounding a flower bed. A different cluster of flowers is planted next to each stone. As you move from one stone to the next you see a whole new cluster. Each is part of the total design. At some point you return to the original cluster. In the cycle of a remedy, these clusters are the fundamental segments of the cycle.

To stretch the metaphor a bit further, different flowers are planted and bloom and die at different times, and there may be others to come up in their place. Like that, the disease is not stationary but continuously flowing, moving, and changing—but only within certain parameters. But one thing is sure—every item that appears in a materia medica must in some way fit into one of those idea clusters, or segments, that make up the total pattern of the remedy. This is why I call it a fundamental segment—fundamental because it is intrinsic and essential, segment because it is a part of the whole cycle.

Another point. Within every remedy you will see certain segments that seem universal, such as weakness. At first this may seem confusing. How can you differentiate between dozens of remedies if they all have segments in common? Easily. The uniqueness of that remedy will be apparent in specifically how that element or segment (weakness) is expressed. Also every remedy will have at least one segment that is somewhat unique unto itself.

However, every symptom of the remedy is not unique and cannot be treated as such, for the vital force is not split in pieces. It strains as one, it reacts as one, and it must be seen as one. This point was made clear by the example of a pregnant woman who said that as soon as she washed her face she began to bleed from the vagina. Now there is no rubric like 'threatened miscarriage from washing the face'. But there is one saying that washing the face causes a nosebleed. This asks the question, "Well, if bathing can cause bleeding in one place, why can't it cause it anywhere?" The location is secondary to the bleeding and to the modality. The remedy chosen, *Arnica montana*, stopped the miscarriage and the child was born healthy. This same principle has been applied to babies who after birth have an epileptic fit when bathed and later are shown to have had a bleed within the brain.

So, at times it is possible, even useful, to generalize a symptom. Boenninghausen was the first to state this point clearly. It is the job of the homeopath to do this kind of generalizing, grouping all symptoms into segments or units that make sense. In most remedies there will be found four to six fundamental segments. Each of these can be broken down into smaller segments, giving even more flavor to the remedy. For example, in the Stramonium cycle presented here, I chose to make hyperactivity into a subsection of the violent overreaction segment.

Once a homeopath understands these clusters of ideas that belong to a remedy, he will easily be able to predict other symptoms that might fit under one segment or another. And he will also be able to predict with some accuracy the rubrics that the remedy should be found in. Thus, the present invention would be invaluable in checking findings as not possible before.

Which Symptoms Go Under which Segment?

The tough part at first is learning how to figure out which rubrics to group together to form each segment in the cycle. Some of the segments will be easier than others to work with. For example, take three different symptoms: a cramp in the abdomen, a cramp in the calf, a twitch in the toe. Although they are in different locations, they are similar in the idea of cramping. So it is easy to see that cramping will be one of the fundamental segments for this patient.

Of course, different homeopaths perceive things differently. Some look for similarities, some look for differences. Some will see cramping and twitching as similar. Some will see them as different. Some will see cramping and obstinacy as similar. That is less obvious. What if you have cramping and twitching and constipation? What do they have in common? Contraction. What about constipation, cramping and obstinacy? This shows that they all are holding on to things. Even though all these symptoms represent the same idea, some will see that and others may not.

Sooner or later a homeopath will have a patient who is sensitive to light, touch and noise, and you will see that what these symptoms have in common is sensitivity. Less obvious but also similar would be sensitivity to noise, aversion to touch, and fear of robbers. Are these similar? Yes, they all represent fear of invasion, another grouping of symptoms. It is almost uncanny how much you can predict with this form of assessing. Not only can you predict symptoms you will find in the patient, but even symptoms you will find in the materia medica.

Some of the fundamental segments or groupings will be more abstract than others. Those will be harder to perceive at first. For instance, what do the following have in common: desire to be rubbed, desires consolation, desire to be carried? Comfort. That one was easy. But what about desire for milk, sweets, pies, ice cream, and fruit? Actually all of them are comfort foods, the kind of foods we seek when we want comforting or when there's an issue of being forsaken. So the homeopath has a patient who is ameliorated by consolation, but when you look up that rubric the remedy the homeopath feels is correct is not there. Every homeopath eventually faces this—finding good rubrics that do not contain the correct remedy. What then? What can be done? Look at the patient's food cravings—one happens to be sweets, a comfort signal. You choose that, simply because you can see in it the same segment you find running throughout, that same emotion of yearning for comfort. And here's where predicting comes in. The homeopath will find many other symptoms in that patient which represent the same idea That same idea must be there, everywhere, because it is a fundamental segment.

Another thing that can be frustrating is getting a great symptom that is rare and peculiar, but there's no rubric for it. Or finding the rubric for that peculiar symptom but lo and behold, the expected remedy is not there (as in the comfort example above). Then what? The cycle of the segments is a way of solving some of these common problems.

The Flow of the Cycle

Once the homeopath sees the relationship of a number of symptoms such as desires consolation, craves sweets, pain better from touch, and ear pain better from being carried, then one has understood one of the fundamental segments in the patient's cycle. Next one has to find out what events caused this to arise in the first place. How did this need for comforting come into being? And what keeps it functioning? And after the homeopath has understood where it came from, the next question is where does it lead the patient? What does it make him do next? The answer to these questions will lead you right into the next segment. Perhaps his need for comfort and consolation makes him overshoot and go into excessive behaviors, outbursts, or some other form of overreaction. If so, you will find similar ideas in the body symptoms that will belong to this group. If the excesses (in this patient) then lead to exhaustion, you have now moved into another segment. And so it goes from one idea to the next to the next, until you come full cycle. At this point the whole cycle will be clear to you.

The job of the homeopath is to keep figuring out how and why each segment leads to something else, or even moves on to a different pathology, but one that shows the same issues, the same elements. One can find a more complete example in The Stramonium Cycle.

These patterns are patterns of the whole person, not just of the mind or the emotions or the body. Some of patients will show the pattern and even tell it in the sequence that matters to them. Other cases will not be so easy because the symptoms may seem so far apart, making it harder to see what they have in common.

For example, a woman was treated who said, "I have thoracic pain that feels like someone is poking at my back ... I am afraid of crowds ... I like to sit on the aisle ... I lock the doors at night." All of these symptoms contain an element of suspiciousness, a feeling of mistrust or doubt, an idea that something is wrong. Even the back pain fit that idea. So it was no surprise that it was necessary to spend another fifteen minutes talking about the remedy and about homeopathy, because of her suspicious nature.

These main ideas that cycle around are the most important thing to look for in the patient. They cycle around, one after another popping up to show the pathology. They are the pathology. Once the homeopath has seen these main ideas or fundamental segments, the next job is to arrange the bulk of the symptoms under each segment. The history and analysis are over and it is time to repertorize.

Practical Application of the Theory

As illustrated by FIG. 2, the visual layout is of a cycle broken by several junctions where symptoms may be listed, with arrows linking one segment to the next.

Figure 3:
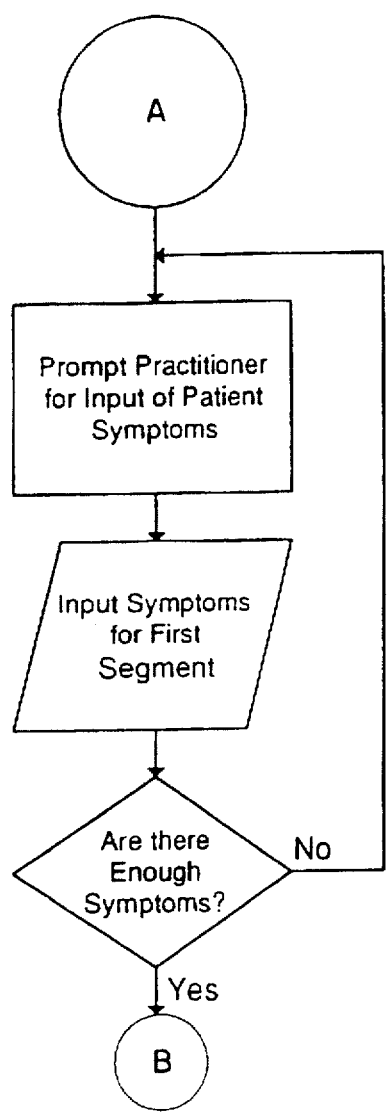
FIGS. 3, 4 and 5 are flow charts of an embodiment of the present invention illustrating the steps of the method.
Figure 4:
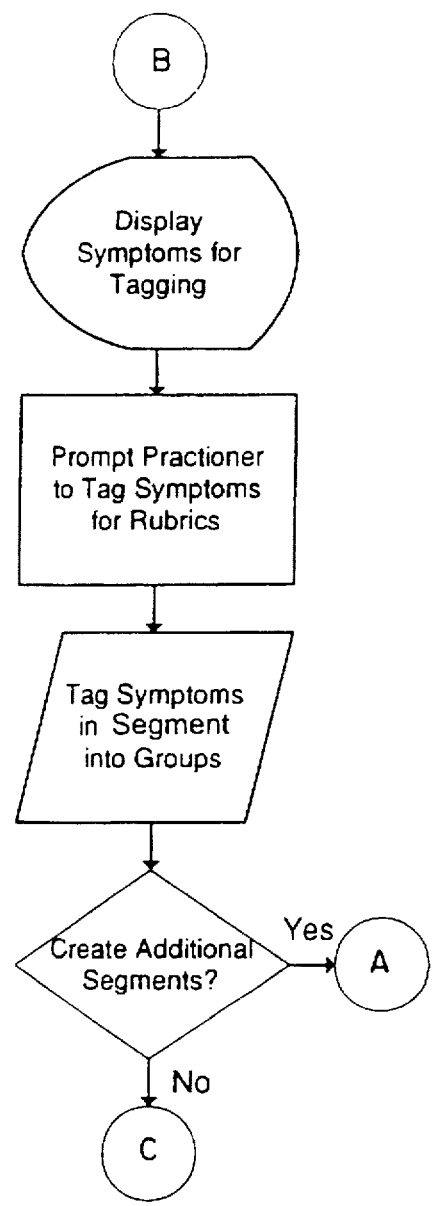
Figure 5:
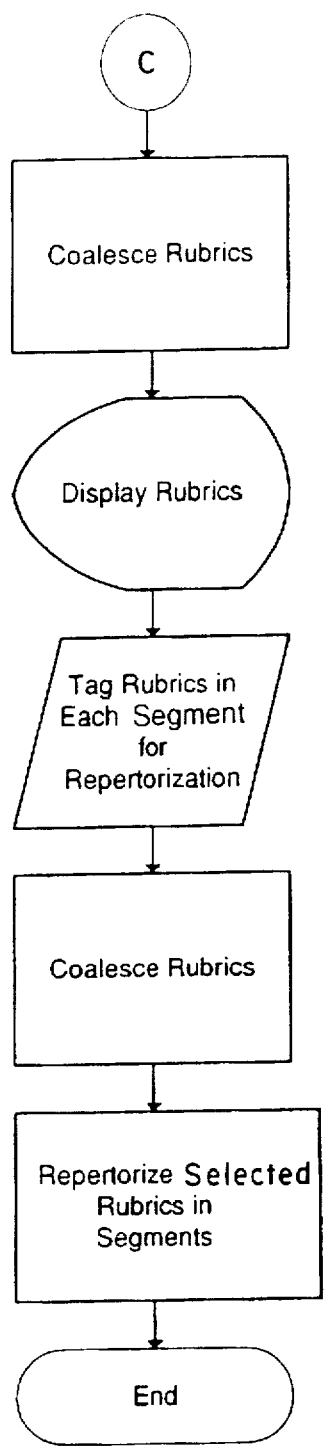

With reference to the flow charts found in FIGS. 3, 4 and 5, the present invention takes pre-existing data, (the repertory.) collates the material to aid in remedy selection. The flow charts illustrate an example of steps performed by an embodiment of the present invention. The present invention also assists the homeopath on the questions necessary to elicit the proper information from the patient. Once collated, the homeopath is able to look at all the symptoms and decide which ones should be used in the analysis.

The system is adapted to allow the homeopath to write the symptoms that the patient describes into the computer in as text. Throughout the case, or after it's finished, depending on preference, the symptoms can be tagged with an identifier such as a number or a letter. Each identifier represent a certain fundamental segment.

Throughout the case, or after it's finished, depending on the users preference, the present invention assists the homeopath separation of the case into fundamental segments. For example, if there are three symptoms of sharp pain in eye, sharp pain in toe, and sharp pain in the rectum; or, bleeding from the nose, bleeding ulcer, black and blue spots. As the patients tells the homeopath the symptoms, they are being recorded and tagged under the homeopath's direction. For instance, those symptoms representing sharp pains are tagged with a segment number, those representing bleeding are also tagged with a different segment number. At the homeopath's discretion, by simply pushing a button the case is separated into fundamental segments utilizing the tagged symptoms.

The case can be stored two ways: the way the case was originally taken as a story, and into fundamental segments.

Once the segments are created, the present invention translates the symptoms into rubrics. Once all the rubrics are listed, the homeopath can select the rubrics for repertorization. By clicking on the rubrics they are automatically designated by the program for repertorization.

With the click of another key, the rubrics are automatically selected in each segment coalesce to become one large rubric per segment, which now contains every remedy within the rubrics selected, all within the same segment. All segments are gone through in the same method.

The user ends by indicating the end of coalescence which begins the search to come up with the remedies that are in common in all the fundamental segments. To find the remedy that is found in each of the segments.

There are other ways of using the program. For example, the patient's complains about a particular problem. The homeopath writes the complaint and tries to discover the most important part of that complaint.

If the answer is very clear, then it will be treated as the first segment. The first symptom found thus far will be the first symptom listed within the first segment.The rubric name may become the name of the segment or a different name may be taken to indicate the general idea of that segment.

The homeopath then asks for other similar complaints, or if anything affects the patient in a similar way. For instance, if a complaint is bleeding gums, and during the course of the interview the patient reveals bleeding in the vagina and rectum. These are all listed under the same segment, which is entitled bleeding. (The answer may turn out to be no, yet the patient also has profuse diarrhea, bleeding from the nose, frequency of urination, and profuse perspiration. Bleeding, it turns out, is not the common segment, instead it would be loss of body fluids.)

Within any segment you may have up to ten symptoms written down. There is a certain criteria of how many to use in the repertorization process. Even though the symptoms are all written down under each segment, they are entered without any value. They are there for reference sake and for understanding. To be included in the repertorization they must be tagged with a code or number. Once they are given a code, all the rubrics with the same number or code within the same segment combine to become one rubric. (This eliminates the difficulty with mistakes and the rubrics being too small and incomplete.)

Generally speaking, one would like to combine it so that the combined number of remedies does not exceed 120 remedies. One might just take one rubric if there were 150 remedies listed, or three rubrics if 40 to 50 listed, or five or six if 15 to 20 were listed in each.

Once the homeopath understands the segment, the computer can prompt to say that homeopath is picking too many rubrics. For instance, if the user of the present invention decided to pick three rubrics within one segment and each one has 150 remedies, the user could be prompted not to pick as many large rubrics, or even as many.

Generally speaking, it is better to pick relatively unrelated rubrics within the same segment. For instance, one mental and one physical within the same segment, or one mental and two physicals from different parts of the body would give you a good representation per segment.

Now that the symptoms are picked and the homeopath understands the rubrics for that segment, the present invention will prompt with questions like:

What does this lead the patient to do?

What are the natural outcomes of this segment?

What can't the patient do?

What does the patient have to do because of this segment?

What does the patient have to do to avoid this segment?

This prompting actually helps to train the doctor in case-taking, and helping the doctor focus the interview into understanding what the second segment is. Therefore, the present invention not only collates and searches but may also function as a aid in training the homeopath to elicit the case.

When the prompting questions are asked the answers will reflect the second segment, which exists because of the first segment. The process renews itself.

The prompts and questions assist the homeopath in asking more questions to understand more and more symptoms that belong in the second segment. The present invention then lists them, translates them into rubrics, and tags the rubrics the homeopath wants to use.

Again the system will prompt the homeopath by asking the questions such as, "what does this lead you to?" The answers to those questions will lead to the third, and then to the fourth segment, and so on.

It's possible that if more than five segments are selected there may be a mistake. To facilitate correction of this situation, the present invention may also ask if one segment represents another. The homeopath would then be able to check and compile the two segments into one.

If the homeopath is stuck, not having completed the cycle, the present invention may prompt with the question, "what led to the first idea, or what situations bring out those symptoms listed in the first segment?" Prompts such as this assist the homeopath in backing into the cycle.

In one embodiment, the screen is divided into two parts. The top lists the remedies that were represented in every one of the segments alphabetically. The bottom lists the smaller remedies, combined salt remedies, and the nosodes that may have come up in all but one or two segments. This allows for a further check to make sure that the remedies that are poorly represented in the repertory do not get lost. The remedies listed can be clicked on and the keynote important symptoms of the remedy pops up for easy reference.

Example Implementation

Figure 6:
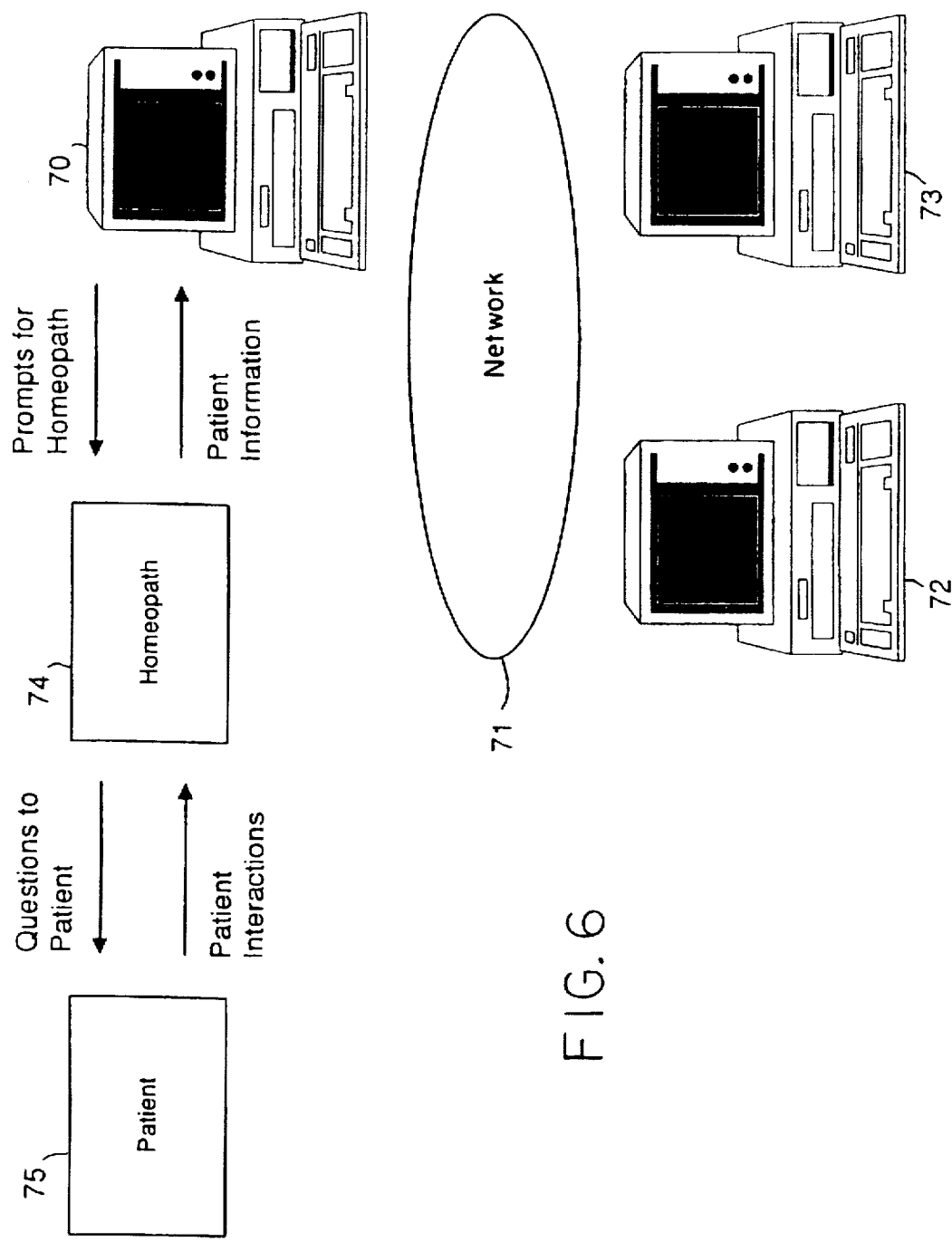
FIG. 6 is a block diagram illustrating an embodiment of the present invention computer
Figure 7:
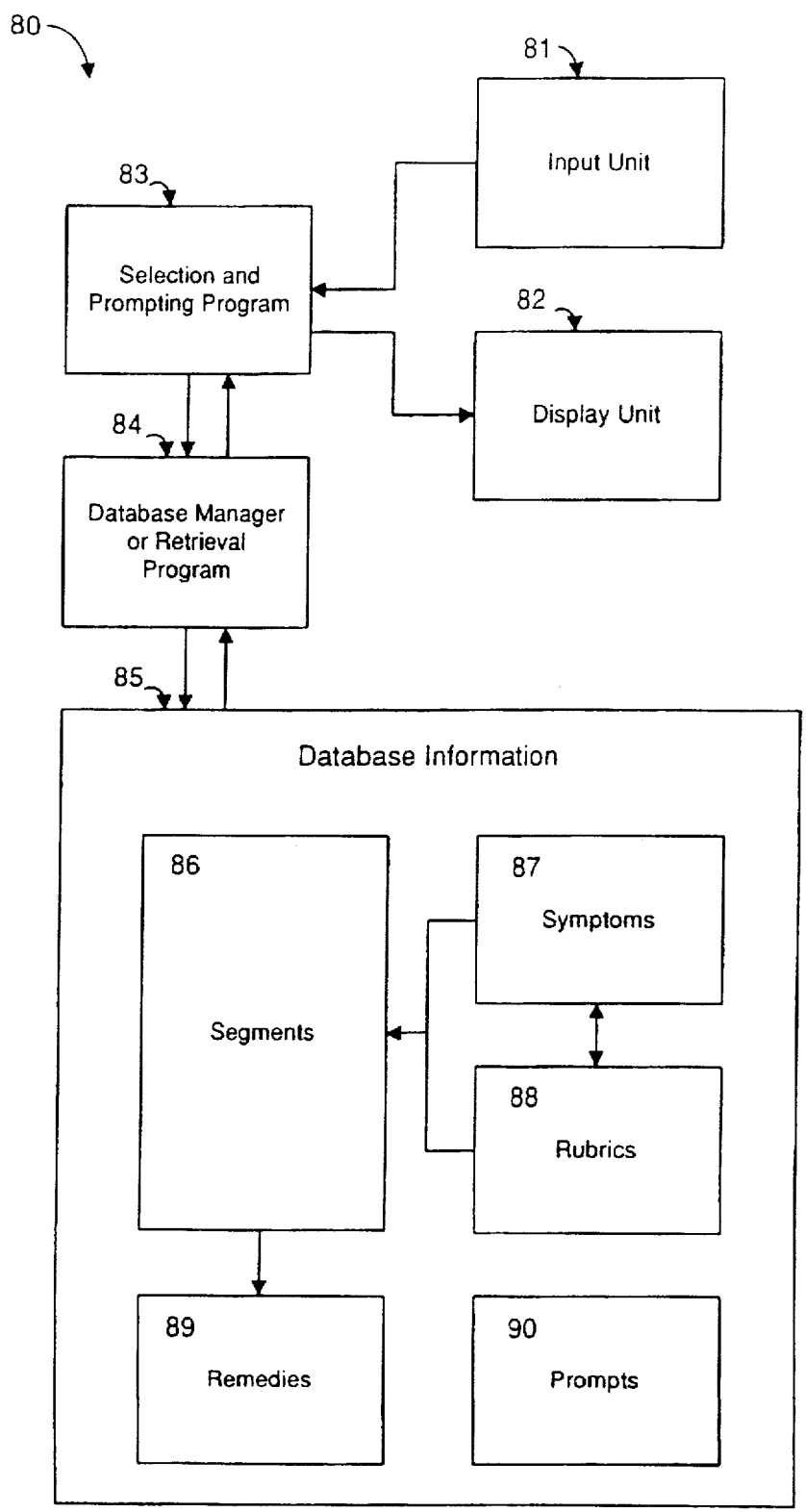
FIG. 7 is a block diagram illustrating the blocks within the computer system of the present invention.

A data processing system 70, suitable for implementing a display system for a medical information system in accordance with the present invention, is illustrated in FIG. 6. The data processing system 70 may be a stand alone computer system or may be a client station 80 and one or more workstations 71 and 72. With reference to FIG. 7, the host or client workstation includes an input unit 81 and an display unit 82. The input unit receives the case-taking information that the homeopath 74 has elicited from the patient 75, and may utilize a conventional keyboard and/or mouse. The display unit 82 is used to display information to the homeopath and would typically be a CRT or printer. The processing system typically contains a main memory (not shown) for holding data which may be used by users of the system. A secondary memory (not shown) is also provided, such as a disk drive, for maintaining the integrity of the database. A processor (not shown) is provided for reading and writing of data from the database stored in memory, and for executing other operations requested by users at other host stations, at workstation.

In the preferred embodiment at the time of filing this application, the workstations and host stations are personal computers such as those manufactured by Apple Computer Corp., Compaq Corp, Dell Computer Corp. These computers may be connected by an I.E.E.E. 802.3 network, and provided with the Microsoft Windows operating system. It should be understood that the invention is not limited by the specific computers, network and operating system shown and described. Other data processing systems may be used in connection with a database to practice this invention. Such a system may be programmed to embody the present invention, such as by using a programming language such as the C++ programming language and its corresponding C++ compiler. As an alternative, or in addition, the system may utilize a database system such as Microsoft Access, also from Microsoft Inc. The database may be used to store and index system information, such as symptoms, rubrics, segments and remedies. In addition, the database may be utilized to store patient information. It should be understood that many other programming languages, compilers and databases are available for this purpose and the invention is not limited thereby.

The computer display system and method of the present invention further includes a database 85 of homeopathic information 86, 87, 88 and 89. In one embodiment of the invention, the database contains a variety of records containing homeopathic information. Specifically, the data records 85 contain symptoms 87, rubrics 88, segments 86 and remedy information 89. The symptom information is related to the rubric information so that a given symptom can reference related rubrics. Rubrics information is related to the segment information so that a given rubric can reference related segments. Rubric and segment information is related to remedy information so that a given rubric or segment can reference related segments.

In a further embodiment of the invention, the database may also contain prompting information 90 to guide the homeopath in use of the system. Prompting records related to symptom, rubric or segment information can contain prompts to facilitate the homeopath in case-taking, rubric identification and segment formation. For instance, if the patient relates a cramp in the abdomen, the symptom can prompt the homeopath to ask about the presence of cramps in other locations. In addition, the system can prompt the homeopath to ask about symptoms related to cramping, such as twitching. In this fashion, the system can prompt the homeopath to probe for additional information.

Figure 8:
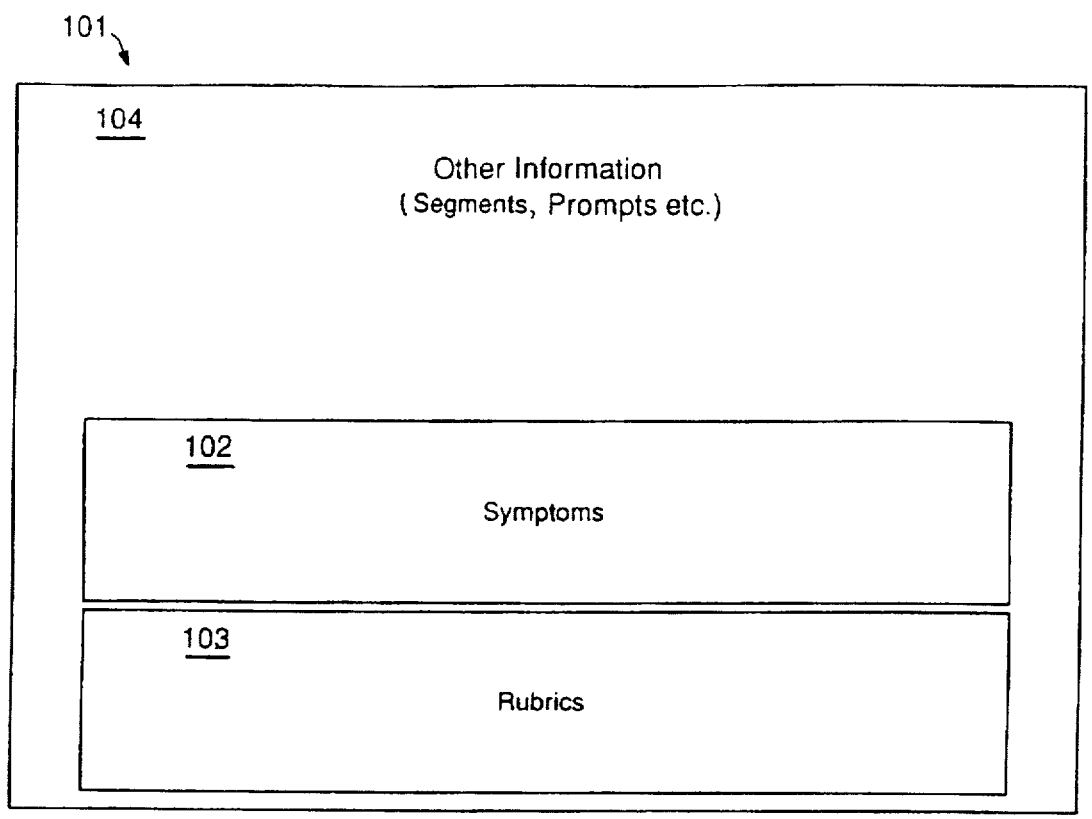
FIG. 8 is a diagram illustrating an example embodiment of the display of the present invention.

The following example illustrates the operation of the system. FIG. 8 illustrates a display 101 of the information utilized to implement the present invention. Display 101 may be divided into fields, such as symptoms field 102 and rubrics field 103. Other fields may be created as required, or fields 102 and 103 may serve multiple purposes. For instance, the symptom field may also display rubric information related to the symptoms. The field 102 may also display segments as they are formed.

Prompting information may also be displayed in area 104 to facilitate case-taking. The location of the fields, and their size, on display 101 is not material to this invention; however it may be preferable to fill the display with the appropriate information for the step under execution by the system. Such information may be displayed graphically. For instance, as segments are build a graphical representation of the segment may be displayed.

The fields 102 or 103 are typically made up of a number of rows. Initially, each row represents a position for entry or display of information. For instance, the homeopath may enter cramp in the abdomen as the first symptom. At this point, the system can index into the database to access prompting records related to the entered symptom. The system then displays in a further datasheet the prompting information from the related records. The homeopath can then utilized the prompting information in questioning the patient.

As additional symptoms for a segment are entered, the system will continue displaying the symptoms and related prompting information. The symptoms are converted by the system into related rubrics. The homeopath can label each of the symptoms/rubrics in a segment with a label, grouping related information by placing the same label on each. At some point, determined either by the homeopath or the system, the symptoms/rubrics may be coalesced into broad rubrics. In this operation, the symptoms, via symptom and/or rubric records, are related through the database to segment records.

At this point, the system may provide additional prompting to the homeopath. The goal is to continue case-taking until a cycle is observed. Once the homeopath observes the cycle, the homeopath tells the system to repertorize the selected segments. The system accesses the remedies related to the identified segments by accessing rubrics included within the segment and then accessing the related remedy records. The system then displays the remedies to the homeopath. At this point, the homeopath may further refine the list of remedies by selecting/deselecting symptoms for specific segments, creating or removing segments or adding symptoms.

The system may further be modified to include storage for patient information including the information just gathered in the case-taking process. Thus, at the conclusion of a case-taking, the homeopath may elect to have the patient information stored within the system. The information thus stored may be recalled at a future date. This aspect of the system assists the homeopath in tracking a course of treatment for each individual patient. For instance, after the initial case-taking, the patient is placed on a course of treatment based upon the remedies selected utilizing the system. In future visits by the patient to the homeopath, the case information is retrieved from the system by the homeopath. By reviewing the retrieved information, the homeopath can determine which of the past recorded symptoms are no longer present, which symptoms are new and modify the case information accordingly. A new set of remedies may then be identified, remedies appropriate for this stage of the disease, by running the current symptoms through the system as done in the initial case-taking. Over time, a historical record of treatments is built for the individual patient, allowing the homeopath closely track and treat the course of the disease.

The system may also be modified to create a set of "segments" based upon the materia medica information stored within the system. This allows the information in the materia medica to be reorganized in a new fashion, unifying related symptoms by criteria other than the physical location of the symptom. For example, rather than listing all of the discharges under each specific body part effected, all discharges can be grouped together. In this way, if a discharge is identified in one location, the system can quickly suggest and prompt the homeopath to look to other locations for similar symptoms. This is additionally helpful in the selection of a remedy. Every homeopathic remedy has a cycle. The system can be modified to also allow the homeopath, upon selection of a particular remedy, to reorganize that remedy into the remedy's underlying cycle. This facilitates the proper selection of remedies by allowing the homeopath to examine the remedy's cycle and compare it to the patient's cycle. In addition, by using the reorganized materia medica information, as the remedy cycle is examined the homeopath can be prompted to look for symptoms related to the remedy cycle.

It is to be understood that many variations on the system are possible. For instance, the information in the records need not be stored in a database system. The user interface may vary by displaying additional information. The system may also be designed to access a remote database.

Having now described embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention as defined by the appended claims.

What is claimed is:

1. A computer-implemented method for facilitating the selection of remedies for a patient, the method implemented on a computer with an input unit, a display unit, a database providing a data file containing a plurality of indexed data records containing symptoms, rubrics, and remedies, the symptom data records containing indications of rubrics, the rubrics containing indications of remedies, the method comprising:

a) receiving via the input unit a first set of input data identifying patient symptoms;

b) receiving via the input unit a first command to create at least one segment consisting of at least one rubric, the segment being associated with a subset of the symptoms;

c) creating the at least one segment by indexing via the database into the data file for a set of rubric data records related to the symptom data records.

d) receiving via the input unit a second command to create at least one remedy from the at least one segment; and e) creating the at least one remedy by indexing via the database into the data file remedy data records indicated by the set of rubric data records in related to the at least one segment.

2. The method of claim 1 further comprising the steps of repeating steps a), b) and c), collecting each at least one segment so created into a set of segments, repeating steps d) and e), and collecting each at least one remedy into a set of remedies for the set of segments.

3. The method of claim 1 further including the step, prior to step a), of prompting, via the display unit, a first set of assisting prompts.

4. The method of claim 1 further comprising the step, after step e), of displaying via the display unit the at least one remedy.

5. A computer-implemented method for facilitating the selection of remedies for a patient, the method implemented on a computer with an input unit, a display unit, a database providing a data file containing a plurality of indexed data records containing symptoms, rubrics, and remedies, the symptom data records containing indications of rubrics, the rubric data records containing indication of remedies, the method comprising:

1) building a set of rubrics until receiving a completion indicator via the steps of
   a) receiving via the input unit a first set of input data identifying patient symptoms,
   b) receiving via the input unit a first command to create at least one rubric from the symptoms,
   c) creating the at least one rubric by indexing via the database into the data file for the symptom data records matching the first set of input data and reading the indications of rubrics in the symptom data record,
   d) collecting the at least one rubric into the set of rubrics;

2) receiving via the input a second command to create at least one segment from the set of rubrics via the steps of
   e) indexing via the database into the data file for rubric data records matching the rubrics in the set of rubrics and collecting the rubric data records into a set of rubric records,
   f) creating via the database an at least one segment data record containing at least a portion of the rubric records, the segment data record representing the at least one segment; and 3) creating the at least one remedy by indexing via the database into the data file for remedy data records related to the at least a portion of the rubric data records in the at least one segment.

6. The method of claim 5 further including the step, prior to step a), of prompting, via the display unit, a first set of assisting prompts.

7. The method of claim 5 further comprising the step, after step 3), of displaying via the display unit the at least one remedy.

8. An apparatus for assisting selection of a homeopathic treatment comprising:

a digital computer;

an input unit connected to the digital computer for inputting data;

an output unit connected to the digital computer for outputting data;

a computer readable memory adapted to store a program for control of the digital computer;

a storage system under control of the digital computer containing data stored in records, the data containing information including symptoms, rubrics, and remedies; and a program in the computer readable memory adapted to control the digital computer to
   prompt, via the output unit, a first set of prompts for input,
   receive a first input containing a set of patient symptoms via the input unit,
   output a second set of prompts for input to identify a major symptom representing a portion of the set of patient symptoms,
   build a first segment representing said major symptom,
   retrieve from the storage system records rubric information related to the first segment,
   retrieve from the storage system records containing remedy information related to the retrieved records containing rubric information, and
   display the information in retrieved remedy records.

9. The apparatus of claim 8, wherein said program is further adapted to build a second segment after building the first segment.

10. The apparatus of claim 9, wherein said program is further adapted to respond to an input instruction by merging said first segment and said second segment into a single segment.

* * * * *